United States Patent [19]

Sawai et al.

[11] Patent Number: 5,155,125

[45] Date of Patent: Oct. 13, 1992

[54] METHOD OF TREATING GASTROINTESTINAL ULCERS WITH SPIRO HYDANTOINS

[75] Inventors: Kiichi Sawai, Funabashi; Masayasu Kurono; Kazumasa Nakano, both of Mie; Makoto Sato, Sofue; Noboru Kuboyama, Mie; Takashi Ito, Gifu; Yoshiya Kondo, Inazawa, all of Japan

[73] Assignee: Sanwa Kagaku Kenkyusho Co., Ltd., Nagoya, Japan

[21] Appl. No.: 600,872

[22] Filed: Oct. 22, 1990

[30] Foreign Application Priority Data

Jan. 12, 1990 [JP] Japan .................................. 2-5773

[51] Int. Cl.⁵ ............................................. A01N 43/50
[52] U.S. Cl. .................................... 514/389; 514/926
[58] Field of Search ............... 514/389, 925, 926, 927

[56] References Cited

U.S. PATENT DOCUMENTS 4,147,795  4/1979  Sarges ................................. 424/273
4,248,882  2/1981  Sarges ................................. 424/273

FOREIGN PATENT DOCUMENTS 0006352  1/1980  European Pat. Off. ............. 233/76

OTHER PUBLICATIONS

Awata et al.,-Chem. Abst. 110(7) 51273 (Feb. 13, 1989) Abst. of Article in *J. Ocul. Pharmacol* 1988.

*Primary Examiner*—Frederick E. Waddell
*Assistant Examiner*—Gregory Hook
*Attorney, Agent, or Firm*—Armstrong & Kubovcik

[57] ABSTRACT

A therapeutic preparation for ulcers contains as a primary ingredient a compound having an aldose reductase inhibitory activity and can accelerate dermal metabolism. That compound may be d-6-fluoro-2,3-dihydro-2',5'-dioxo-spiro [4H-1-benzopyran-4,4'-imidazolidine]-2-carboxyamide, d-2-chloromethyl-6-fluoro-2,3-dihydro-spiro [4H-1-benzopyran-4,4'-imidazolidine]-2',5'-dione and d-2-bromomethyl-6-fluoro-2,3-dihydro-spiro [4H-1-benzopyran-4,4'-imidazolidine]-2',5'-dione.

1 Claim, No Drawings

METHOD OF TREATING GASTROINTESTINAL ULCERS WITH SPIRO HYDANTOINS

BACKGROUND OF THE INVENTION

1. Field of the Invention

The present invention relates to a therapeutic preparation for ulcers containing an aldose reductase as a primary component. In particular, this invention provides an externally administrated therapeutic preparation for labial and dermal ulcers, corrosive wounds, bed sores (decubitus), burns, frostbite and scleroderma and an internally administered therapeutic preparation for intra-oral and gastrointestinal tract ulcers.

2. Prior Art

In recent years, it has been found that one of causes for cataract, retinitis and various nervous disorders induced by diabetes is an intracellular accumulation of sorbitol by way of a polyol path, and attention has been paid to various aldose reductase inhibitory substances, because an enzymatic inhibition in association with the exchange between aldose and polyol reduces the production or accumulation of sorbitol.

The applicant has already filed patent applications for the compounds used for this invention (see Japanese Patent Kokai Publication No. 61(1986)-200991 and U.S. Pat. No. 4,861,792).

Heretofore, many aldose reductase inhibitors have been studied for treating diabetic complications (see U.S. Pat. No. 4,900,739). However, never until now is it known that aldose reductase inhibition systems take part in the promotion of tissue metabolism and have an effect upon inhibiting ulceration as well.

SUMMARY OF THE INVENTION

According to one aspect of this invention, the aldose reductase inhibitor includes a compound having an aldose reductase inhibitory activity, such as those available in the form of pharmaceutical preparations, for instance, Sorbinil (CAS 68367-52-2), Epalrestant (CAS 82159-09-9) and Ponalrestant (CAS 72702-95-5) now commercialized or under development. However, preference is given to a hydantoin compound.

According to another aspect of this invention, there is provided a preparation composition which contains an aldose reductase inhibitory substance, esp., an optically active type of hydantoin derivative and which, whether of an internal administration type or an external administration type, is well-absorbed in ulcerated regions after administration.

DETAILED EXPLANATION OF THE INVENTION

The hydantoin compounds used in this invention include an optically active type of hydantoin derivatives expressed by the following general formula:

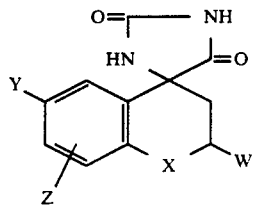

wherein:

W stands for a halogenomethyl group, a 1H-tetrazol-5-yl group, a —COOR group in which R is a hydrogen atom, an alkyl group or a —(CH$_2$CH$_2$O)$_n$CH$_3$ group in which n means an integer of 1–113 or a substituted phenyl group;

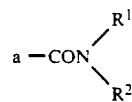

group in which $R^1$ and $R^2$, which may be identical with or different from each other, each stand for a hydrogen atom, an alkyl group, a —(CH$_2$CH$_2$O)$_n$CH$_3$ group in which n means an interger of 1–11 or a substituted phenyl group, or alternatively $R^1$ and $R^2$ may form a 5 or 6-membered heterocyclic ring together with a nitrogen atom or other nitrogen atom or oxygen atom; a —CH$_2$OR$^3$ group in which $R^3$ means a hydrogen atom or an alkyl group; or a

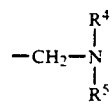

group wherein $R^4$ and $R^5$, which may be identical with or different from each other, each mean a hydrogen atom or an alkyl group, X means an oxygen or sulfur atom, and Y and Z, which may be identical with or different from each other, each means a hydrogen atom or a halogen alkyl, alkoxy or alkylmercapto group. Particular mention is made of d-6-fluoro-2,3-dihydro-2',5'-dioxo-spiro [4H-1-benzopyran-4,4'-imidazolidine]-2-carboxyamide, d-2-chloromethyl-6-fluoro-2,3-dihydro-spiro [4H-1-benzopyran-4,4'-imidazolidine]-2',5'-dione and d-2-bromomethyl-6-fluoro-2,3-dihydro-spiro [4H-1-benzopyran-4,4'-imidazolidine]-2',5'-dione. If desired, the hydantoin derivatives may be provided in the form of a composition to which stabilizers, absorption accelerators are added. Preparative carriers used may be carboxylmethylcellulose, polyvinyl pyrrolidone, cyclodextrin, etc.

The therapeutic preparations according to this invention activate tissue metabolism and so are efficacious against all aspects of exhaustion tissue necroses including intraoral and dermal ulcers.

The present preparations are particularly efficacious against one of the aspects of exhaustion tissue necroses, esp., cuticular ulcers such as senile and traumatic decubiti, to say nothing of diabetic decubitus. Besides, they are useful for treating burns, frostbite and scleroderma.

The present preparations are also administrable to labial, gastrointestinal tract and defective tissue ulcers.

The present invention will now be explained more specifically but not exclusively with reference to pharmacological tests and examples.

EXAMPLES

Preparation Examples

Three hydantoin derivatives, i.e., d-6-fluoro-2,3-dihydro-2',5'-dioxo-spiro [4H-1-benzopyran-4,4'-imidazolidine]-2-carboxyamide (hereinafter called Compound A), d-2-chloromethyl-6-fluoro-2,3-dihydro-spiro [4H-1-benzopyran-4,4'-imidazolidine]-2',5'-dione hereinafter called Compound B) and d-2-bromomethyl-6-fluoro-2,3-dihydro-spiro [4H-1-benzopyran-4,4'-imidazolidine]-2',5'-dione (hereinafter called Compound C) are used to obtain preparations (a) ointment, (b) liquid for external administration, (c) cream, (d) suppository and (e) tablet.

| (a) Ointment | |
|---|---|
| Compound A is dispersed in a ten-fold amount of cyclodextrin | 100 g |
| 25% hydrolyzed lanolin | 600 g |
| White petrolatum | 300 g |
| Total: | 1000 g |

The above-mentioned components are mixed together to prepare an ointment containing 10 mg of Compound A per 1 g.

| (b) Liquid for external administration (Emulsifiable lotion) | |
|---|---|
| Compound B | 1.0 g |
| Carboxymethylcellulose | 0.5 g |
| Stearyl alcohol | 2.5 g |
| Liquid paraffin | 20.0 g |
| Sodium lauryl sulfate | 1.0 g |
| Propylene glycol | 17.0 g |
| Methyl p-hydroxybenzoate | 0.025 g |
| Propyl p-hydroxybenzoate | 0.015 g |
| Purified water | balance |
| Total: | 100.0 ml |

Liquid paraffin is added to stearyl alcohol dissolved on a water bath. Afterwards, the solution is heated to 70 (an oil layer). The remaining components, on the other hand, is added to hot water, which is then held at 70 to prepare a water layer.

The water layer is added to the oil layer, and the resulting solution is cooled down to 45 under agitation and cooled off, thereby obtaining an emulsifiable lotion.

| (c) Cream | |
|---|---|
| (Layer A) | |
| Polyoxyl 40 stearate | 50 g |
| Glycerin fatty acid ester | 140 g |
| Tallow fatty acid glyceride | 70 g |
| Cetanol | 60 g |
| Butyl p-hydroxybenzoate | 1 g |
| (Layer B) | |
| Compound C | 10 g |
| Propylene glycol | 50 g |
| Methyl p-hydroxybenzoate | 1 g |
| 3% aqueous solution of albumin | 100 g |
| Purified water | balance |
| Total (A + B): | 1000 g |

The layers A and B are separately heated to 70–80. While the layer A is stirred, the layer B is gradually added thereto. The product is stirred at 45 under reduced pressure, and then cooled off to obtain a desired cream.

| (d) Suppository | |
|---|---|
| Compound A | 100 mg |
| Cacao butter | 1600 mg |

| (d) Suppository -continued | |
|---|---|
| | 1700 mg per suppository |

Compound A is dispersed in a cacao butter (higher fatty acid glyceride) melt that is an oil and fat base, and then formed in conventional manners to obtain suppositories.

| (e) Tablet | |
|---|---|
| Compound A | 50 g |
| Sodium citrate | 25 g |
| Arginine | 10 g |
| Polyvinyl pyrrolidone | 10 g |
| Magnesium stearate | 5 g |

In conventional manners, the above-mentioned components are tableted to prepare 1000 tablets for oral administration, each containing 50 mg of the active component.

PHARMACOLOGICAL TEST EXAMPLE 1

Effect on Inhibiting Ulcer Induced by Water Immersion Stress

After 24-hour fasting, S.D. musculine rats weighing 250–270 g were immersed to their breasts in a water tank maintained at 23 1 to load a water immersion stress on them. Seven hours later, the stomachs were evulsed and filled with 10 ml of a 2% formalin solution according to the method described in "Jap. J. Pharmac.", 18, pp. 9–18 (1968) for temporal fixation. The stomachs were incised to find the sum of lenghts of ulcerated regions on the bodies of stomach—an ulcer factor. A solution of 20 mg/kg of the instant compound dissolved in physiological saline was orally administrated to the animals 10 minutes before stress loading.

As reported in Table 1, the instant compound showed an inhibitory action upon the ulceration of the stomach bodies.

TABLE 1

| | Number of animals | Ulcer Factor |
|---|---|---|
| Control Group | 10 | 14.8 2.0 |
| Compound | | |
| A | 10 | 11.5 1.5 |
| B | 10 | 10.6 1.2 |
| C | 10 | 12.2 2.6 |
| Sorbinil | 10 | 12.6 1.8 |

PHARMACOLOGICAL TEST EXAMPLE 2

Effects on Treating Dermal Ulcer and Frostbite

S.D. rats weighing about 50 g (3 for each group) were used as test animals. The animals were fed with a 30% galactose-containing powder feed. After the lapse of four weeks, their skins were grained and torn off over an area of 1 cm$^2$ along their regions' lines. At the same time, a dry ice mass of 0.5 cm$^3$ was bonded to each animal 2 cm below the root of the tail to get it frostbitten over an area of about 1 cm$^2$ at the second or third degree. The animals were subsequently fed with normal and galactose feeds to examine an influence of the accumulation of galactitol upon dermatoplasty.

The frostbitten regions were all applied with a procaine penicillin G liquid to protect them against bacterial infection, etc. The test group of animals was applied with an ointment according to Preparation Example (a) daily for one week after frostbitting and thereafter every two days. After slaugter, the frostbitten regions were observed as to their cure degree.

The cure degree was estimated in terms of the following ranks:

+++: the wounds were all well-cured.
++: most of the wounds were cured.
+: the wounds did not get worse.
−: at least one of the wounds got worse.

How much the animals were frostbitten was estimated in terms of the following degrees:

Second degree: an erosion with broken blisters
Third degree: a browning of the tissue
Fourth degree: a wound reaching the bone The cure degree of frostbite was estimated by comparing the dermal strength of the wounds with an average strength of the control group. Referring to the second degree cases of frostbite, on the one hand, +++ indicates that all the test animals attains superiority over the control animals and ++ indicates that most of the test animals attains superiority over the control animals. Referring to the 3rd degree cases of frostbite, on the other hand, + indicates that the wounds did not get worse, although they were similar in degree to those of the control group and − indicates that at least one of the wounds got worse.

A) Cure Degree of Wound (Dermal Ulcer)

Set out in Tables 2 and 3 are the results, from which it is found that the in vivo accumulation of galactitol does not only give rise to a difference in the cure degree of frostbite but has an adverse influence on dermatoplasty, and that the aldose reductase inhibitor can remarkably accelerate dermatoplasty on wounds.

TABLE 2

| (Cure Degree of Wound) | |
|---|---|
| Normally fed rats | |
| (1) Untreated | ++ |
| (2) Treated with ointment | +++ |
| Continuously fed rats with galactose | |
| (3) Untreated | − |
| (4) Treated with ointment | ++ |
| Rats which were fed with galactose and normal feed after wounded | |
| (5) Untreated | − |
| (6) Treated with ointment | + |

TABLE 3

| (Cure Degree of Frostbite) | | |
|---|---|---|
| | Degree of Frostbite | Cure Degree |
| Normally fed rats | | |
| (1) Untreated | 2 | control |
| (2) Treated with ointment | 2 | +++ |
| Galactose-fed rats | | |
| (3) Untreated | 3 | − |
| (4) Treated with ointment | 3 | ++ |
| Rats which were fed ith galactose and normal feed after frostbitten | | |
| (5) Untreated | 3 | − |
| (6) Treated with ointment | 3 | + |

USE EXAMPLE 1

The instant example was carried out by having 8 volunteers use the cream preparation (c) optionally, who suffered from urtication, paralysis and xeroderma at their limbs in cold weather. One month later, questionnairing was conducted on whether the conditions got better or worse. The results are as follows.

| Better | 7 |
|---|---|
| Stayed the same | 1 |
| Worse | 0 |

USE EXAMPLE 2

One (1) g of Compound A was dissolved in 100 ml of physiological saline with cyclodextrin to obtain a cough preparation.

The instant example was carried out by having three volunteers drink this preparation, who took cold and became inflammed in their throats. Later, questionnairing was conducted on whether the conditions got better or worse about the following four points. The results are set out below.

| | Better | Stayed the same | Worse |
|---|---|---|---|
| (a) A pain in the throat | 3 | 0 | 0 |
| (b) Feeling thirsty | 3 | 0 | 0 |
| (c) A chopping on the lip | 2 | 1 | 0 |
| (d) A swelling and pain in the mouth and the gum | 1 | 2 | 0 |

We claim:

1. A method for treating ulcers of the stomach and gastrointestinal tract which comprises orally administering to an animal in need of such treatment and antiulcer effective amount of a compound selected from the group consisting of d-6-fluoro-2,3-dihydro-2',5'-dioxo-spiro[4H-1-benzopyran-4,4'-imidazolidine]-2-carboxyamide, d-2-chloromethyl-6-fluoro-2,3-dihydro-spiro[4H-1-benzopyran-4,4'-imidazolidine]-2',5'-dione and d-2-bromomethyl-6-fluoro-2,3-dihydro-spiro[4H-1-benzopyran-4,4'-imidazolidine]-2',5'-dione.

* * * * *